United States Patent
Gazley

(10) Patent No.: US 8,545,810 B2
(45) Date of Patent: Oct. 1, 2013

(54) METHODS AND COMPOSITIONS FOR TREATMENT OF ADD/ADHD, DEPRESSION, MEMORY PROBLEMS AND OTHER CONDITIONS

(76) Inventor: Jef Gazley, Scottsdale, AZ (US)

(*) Notice: Subject to any disclaimer, the term of this patent is extended or adjusted under 35 U.S.C. 154(b) by 0 days.

(21) Appl. No.: 13/314,112

(22) Filed: Dec. 7, 2011

(65) Prior Publication Data

US 2012/0082620 A1    Apr. 5, 2012

Related U.S. Application Data

(62) Division of application No. 12/214,175, filed on Jun. 16, 2008, now abandoned.

(60) Provisional application No. 61/016,339, filed on Dec. 21, 2007, provisional application No. 60/944,066, filed on Jun. 14, 2007.

(51) Int. Cl.
*A61K 49/00* (2006.01)
*A61K 36/714* (2006.01)
*A61P 25/00* (2006.01)
*A61P 25/24* (2006.01)

(52) U.S. Cl.
USPC ............ 424/9.1; 424/725; 424/643; 424/752; 424/682

(58) Field of Classification Search
USPC ............................ 424/9.1, 725, 643, 752, 682
See application file for complete search history.

(56) References Cited

U.S. PATENT DOCUMENTS

| | | | |
|---|---|---|---|
| 4,352,796 A | 10/1982 | Arichi et al. | |
| 4,857,321 A | 8/1989 | Thomas | |
| 4,874,793 A | 10/1989 | Franks | |
| 5,290,784 A | 3/1994 | Qu et al. | |
| 5,391,372 A | 2/1995 | Campbell | |
| 5,599,561 A | 2/1997 | Gonzalez, Jr. | |
| 5,766,596 A | 6/1998 | Kwon | |
| 5,882,648 A | 3/1999 | Yoshihara et al. | |
| 6,294,520 B1 | 9/2001 | Naito | |
| 6,641,801 B1 | 11/2003 | Brown | |
| 6,896,898 B1 | 5/2005 | Xiong et al. | |
| 6,955,873 B1 | 10/2005 | Blum | |
| 2002/0151802 A1 | 10/2002 | Lowen et al. | |
| 2005/0042271 A1 | 2/2005 | Xiong et al. | |
| 2006/0088575 A1 | 4/2006 | Brewitt | |
| 2006/0217365 A1 | 9/2006 | Davis et al. | |

OTHER PUBLICATIONS

Bensky et al., "Chinese Herbal Medicine Materia Medica," Eastland Press, p. 299 (1986).
De Schepper, Luc MD, "LM Potencies," Simillimum, XIII:45-65 (2000).
Murphy, R. ND, "Hahnemann's Water Potencies," The Organon and LM Prescribing, p. 133-138 (1993).
Ullman, D., "Ten Most Frequently Asked Questions on Homeopathic Medicine," Townsend Letter for Doctors & Patients, pp. 20-21 (Oct. 1999).

(Continued)

*Primary Examiner* — Ernst Arnold
*Assistant Examiner* — Hong Yu
(74) *Attorney, Agent, or Firm* — Fennemore Craig, P.C.

(57) ABSTRACT

Disclosed herein are compositions and methods for treating a variety of mood and behavioral disorders, including attention deficit hyperactivity disorder (ADHD), anxiety, depression, memory loss, as well as other conditions. Also disclosed herein are methods for diagnosing certain conditions, such as ADHD, using these compositions.

14 Claims, 6 Drawing Sheets
(6 of 6 Drawing Sheet(s) Filed in Color)

(56) References Cited

OTHER PUBLICATIONS

Author Unknown, "Aconitum heterophyllum/Ativisha/Cao wu/Tsau wu," [Online], [retrieved on May 9, 2007]. Retrieved from the Internet: <URL:http://herbal-remedies=usa.stores.yahoo.net/aconitum-information.html>.

Author Unknown, "Aconite Homeopathic Clikpak, 30C-84 Pellets," [Online], [retrieved on May 9, 2007]. Retrieved from the internet: <URL:http://herbal-remedies-usa.stores.yahoo.net/anxiety-pills.html>.

Author Unknown, "Nature's Sunshine Online Catalog ADD & ADHD Brain Food," [Online], [retrieved on May 9, 2007]. Retrieved from the internet: <URL:http://www.theherbsplace.com/ADD_ADHD_Brain_Food-page_1_c_75.html>.

Author Unknown, "Attention Deficit Disorder/ADD/ADHD Information," [Online], [retrieved on May 9, 2007]. Retrieved from the internet: <URL:http://herbal-remedies-usa.stores.yahoo.net/add.html>.

Author Unknown, "Pycnogenol," [Online], [retrieved on May 9, 2007]. Retrieved from the internet: <URL:http://www.herbindex.net/pycnogenol.html>.

Author Unknown, "What are the medicines?", [Online], [retrieved on May 9, 2007]. Retrieved from the internet: <URL:http://www.homeopathic.org/meds.htm>.

Author Unknown, "Stress-J," [Online], [retrieved on May 9, 2007]. Retrieved from the internet: <URL:http://www.theherbsplace.com/Stress_J_p_260.html>.

Author Unknown, "How are the remedies prescribed?", [Online], [retrieved on May 9, 2007]. Retrieved from the internet: <URL:http://www.homeopathic.org/prescribe.htm>.

Author Unknown, "Homeopathic Treatments for ADHD," [Online], [retrieved on Mar. 20, 2007]. Retrieved from the internet: <URL:http://www.healing-arts.org/children/ADHD/homeopathy.htm>.

Author Unknown, "*Aconitum napellus* (Wolfsbane)," [Online], [retrieved on Mar. 20, 2007]. Retrieved from the internet: <URL:http://www.vaxa.com/ingredients/Aconitum-napellus.cfm>.

Author Unknown, "Attention Deficit Disorder," [Online], [retrieved on Mar. 20, 2007]. Retrieved from the internet: <URL:http://www.upmc.com/HealthManagement/ManagingYourHealth/HealthReference/Diseases/InDepth/?chu . . .>.

Author Unknown, "Aconite General Information," [Online], [retrieved on Mar. 20, 2007]. Retrieved from the internet: <URL:http://www.herbalremedies.com/aconite-information.html>.

Author Unknown, "Herbal/Plant Therapies: Pycnogenol (*Pinus pinaster* ssp. atlantica)," [Online], [retrieved on Mar. 20, 2007]. Retrieved from the internet: <URL:http://www.mdanderson.org/departments/cimer/display.cfm?id=8ca896e2-ff36-4f2b-a51c97db574f51 c9& . . .>.

Author Unknown, "Attend—Ingredients," [Online], [retrieved on Mar. 20, 2007]. Retrieved from the internet: <URL:http://www.add-attend.com/add_attend_ingredients.shtml>.

Author Unknown, "Attend—General Information," [Online], [retrieved on Mar. 20, 2007]. Retrieved from the internet: <URL:http://www.add-attend.com/add_attend_general_information.shtml>.

Author Unknown, Excerpt from Lotus Health Institute website, "Hahnemann's LM and Water Potencies,"[Online] [retrieved on May 28, 2010]. Retrieved from the Internet: <URL:http://www.alchemilla.com/index.php?option=com_content&view=article&catid=13%3Ahomeopathic-literature&id=14%3Ahahnemanns-lm-and-water-potencies&Itemid=33>.

METHODS AND COMPOSITIONS FOR TREATMENT OF ADD/ADHD, DEPRESSION, MEMORY PROBLEMS AND OTHER CONDITIONS

CROSS-REFERENCE TO RELATED PATENT APPLICATIONS

This patent application is a divisional of U.S. patent application Ser. No. 12/214,175, filed Jun. 16, 2008, and is based on and claims the benefit of U.S. Provisional Application Ser. Nos. 61/016,339 filed Dec. 21, 2007 and 60/944,066 filed Jun. 14, 2007, the content of each of which is incorporated herein in its entirety by reference thereto.

FIELD OF THE INVENTION

The present invention comprises methods and composition for treatment a variety of neurological and behavioral health conditions, including:
  A. Attention Deficit Disorder (also known as Attention Deficit Hyperactivity Disorder, and referred to herein as "ADD/ADHD");
  B. Depression;
  C. Anxiety/Agitation;
  D. Memory disorders, including but not limited to Alzheimer's Disease;
  E. Menopausal symptoms, including but not limited to depression, loss of energy, loss of focus/concentration, etc.;
  F. Obsession, including obsessive-compulsive disorder;
  G. Sleep disorders, including but not limited to insomnia;
  H. Prostate and bladder dysfunction; and
  I. Dysfunctions in sexual performance and/or decrease in sexual desire (aphrodisiac uses).

BACKGROUND OF THE INVENTION

There is an increasing awareness in our society, particularly amongst physicians, psychologists, social workers, counselors, other health care professionals, and other types of professionals, of various behavioral and mood disorders which affect an individual's ability to function efficiently and feel satisfied with life. Behavioral and mood disorders can range from mild to severe, and can interfere with an individual's daily life, including the individual's ability to earn a living, earn an education, carry out social and familial relationships, and carry out the tasks of daily life. Behavioral and mood disorders can occur at any age, and thus individuals requiring treatment can range from young children through the elderly.

Professionals in the field of mental and behavioral health tend to utilize a wide range of therapies to treat individuals having behavioral and/or mood disorders. For example, cognitive therapy, behavior therapy, play therapy, and psychotherapy are types of therapy that may be used. In addition to or in lieu of the aforementioned therapies, medications are often administered. It is commonplace for professionals to treat mental and behavioral health issues with pharmaceuticals, particularly orally administerable ones or those administerable via transdermal patches, with the goal of better assisting the brain in functioning, such as by effecting the neurotransmitter chemicals in the brain, or by other means, some of which are not clearly understood.

There is a growing interest in utilizing so-called alternative medicine, including but not limited to nutritional intervention to treat behavior and/or mood disorders. In particular, many individuals are increasingly utilizing herbal supplements, amino acid supplements such as fish oil and evening primrose oil, to treat and prevent a variety of conditions. Such nutritional supplements are often, but not always, associated with lower undesirable side effects than traditional pharmaceutical treatments, and sometimes are as effective or even more effective than traditional treatments. Nutritional supplements may also be used in combination with traditional pharmaceutical treatments. Accordingly, many individuals have found success treating mental and behavioral health issues using nutritional supplements.

Many health care professionals such as physicians incorporate into their practices such non-traditional or so-called "alternative" treatments. One type of alternative treatment that is widely accepted amongst naturopathic physicians is homeopathy.

Homeopathy is a system originated in the late eighteenth century, for the treatment of individuals afflicted with certain conditions or disease, and involves the administration of minute doses of a substance, that in massive amounts produces symptoms in healthy individuals similar to those of the disease itself. Homeopathy is based on the idea that substances that produce symptoms of sickness in healthy people will have a curative effect when given in very dilute quantities to sick people who exhibit those same symptoms. Homeopathic remedies are believed to stimulate the body's own healing processes. One of the basis tenets of homeopathy is that small amounts of the substance are helpful, and that as the amount of the substance is increased, the less helpful and more deleterious the effect on the patient.

Homeopathic remedies are generally produced via iterated shaking and dilution, in ethanol or in water, from a starting substance. For example, to produce a homeopathic remedy of a particular plant substance, the plant substance is first mixed in alcohol to obtain a tincture. One drop of the tincture is then mixed with 99 drops of alcohol (to achieve a ratio of 1:100) and the mixture is strongly shaken. This shaking process is known as succussion. The final bottle is labeled as "1C". One drop of this 1C is then mixed with 100 drops of alcohol and the process is repeated to make a 2C. The process is again repeated, to make a 3C. By the time the 3C is reached, the dilution is 1 part in 1 million. Thereafter, tiny globules or pellets made from sugar are then saturated with the 3C liquid dilution. These pellets constitute the homeopathic medicine.

To prepare a 6× potency successsion, one part of the herbal mother tincture is combined in a vial with nine parts of the carrier liquid, and succussed ten times again, making a 2× solution. The process is repeated four more times, for a total of six dilutions and succussions- and the final result is a 6× potency of the herb. Pellets are then saturated with the 6× potency succession.

A practitioner of homeopathy would expect that administering to a subject 1 pellet of a 6× formula would have the same effect (qualitatively and quantitatively) on the condition treated than if one were to administer 5 pellets of a 6× formula. In contrast, the present invention demonstrates the opposite. Although it utilizes homeopathic pellets, the present invention is based at least in part on the discovery that administering 5 pellets of 6× is indeed significantly more beneficial in treatment of conditions such as ADD/ADHD than if one were to administer only 1 6× pellet. This challenges a core tenant of homeopathy.

The present invention utilizes homeopathic techniques, but is based in part on the surprising discovery that one may successfully treat certain mood and behavioral conditions by orally administering certain dosages of homeopathic pellets above what homeopathic theory teaches.

BRIEF SUMMARY OF THE INVENTION

Disclosed herein are compositions and methods for treating a variety of mood and behavioral disorders, including attention deficit hyperactivity disorder (ADHD), anxiety, depression, memory loss, as well as other conditions. Also disclosed herein are methods for diagnosing certain conditions, such as ADHD, using these compositions.

BRIEF DESCRIPTION OF THE SEVERAL VIEWS OF THE DRAWINGS

The patent or application contains at least one drawing executed in color. Copies of this patent or patent application publication with color drawing(s) will be provided by the Office upon request and payment of the necessary fee.

DETAILED DESCRIPTION OF THE INVENTION

Figures 1A, 1B, 1C:
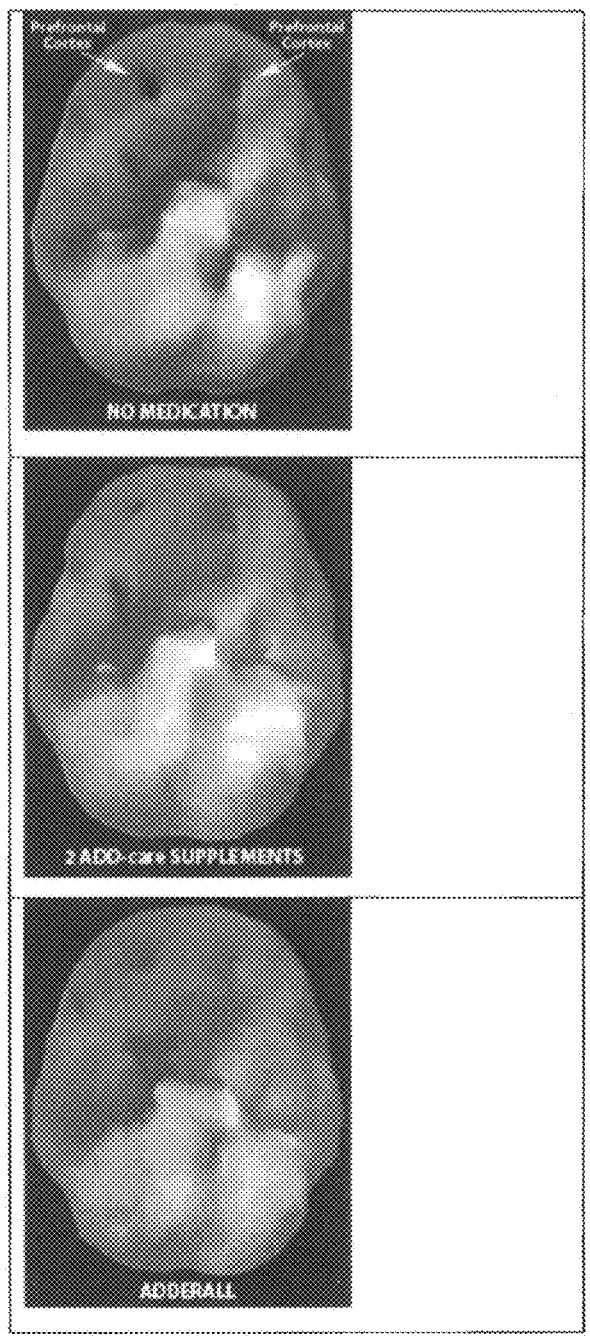
FIGS. 1A-1F illustrate a series of SPECT scans of a 36 year old female human subject, showing the effects of treatment according to the invention and according to the prior art.

The present invention relates to compositions for the diagnosis and/or treatment of a variety of behavioral and mental health issues. The compositions appear to be safe and effective, and do not appear to result in undesirable side effects.

The composition comprises: homeopathic pellets of Aconite. Aconite is an herb obtained from the Monkshood plant in the Genus of *Aconitum*. Preferred species of Aconite for use in the present invention are *Aconitum napellus* and *Aconitum carmichaeli*.

More specifically, the homeopathic pellets are preferably of at least 3× or greater strength. By "3× or greater" it is meant dilutions of 4×, 5×, 6×, 7×, etc. (i.e., the 4× is more highly diluted than the 3×, but the 4× is considered according to homeopathy to be of greater strength). Still more preferably the homeopathic pellets are 5×.

In one preferred embodiment, the composition consists essentially of homeopathic pellets of Aconite, such as of *Aconitum napellus* or *Aconitum carmichaeli*. Preferably, the pellets are 6×. Although satisfactory results are achieved using only the aforementioned homeopathic pellets, it is possible to enhance the treatment effects of the composition by including additional components. The additional components used will depend upon the condition to be treated.

The additional components include supplements, such as herbal supplements, vitamin and/or mineral supplements, and/or amino acid supplements. These supplements may be chosen from the following, but are not limited to: GABA, L-Tyrosine, L-5HTP, pycogenol, DMAE, Gingko biloba, Gotu kola, Guarana, Magnesium, Zinc, etc.

The compositions are for oral administration, preferably in capsule form. Typically, each administration is of 1-3 capsules, wherein each capsule contains at least 3 pellets of 3× Aconite. Still more preferably, it is administered in the amount of 1-3 capsules, each containing 5 pellets of 6× Aconite.

Examples of specific behavioral and mental health issues that may be diagnosed and/or treated according to the invention are discussed below.

A. Attention Deficit Disorder, also known as Attention Deficit Hyperactivity Disorder ("ADD/ADHD")

The present invention relates to methods and compositions useful for the diagnosis and treatment of ADD/ADHD as follows:

1. A method of diagnosing ADD/ADHD by determining whether a human subject's electrical system or nervous system's polarity switches from contralateral to homolateral.

2. A method of treating ADD/ADHD, to temporarily alleviate and/or eliminate symptoms in a human subject exhibiting such symptoms, comprising administering a composition containing at least one herb of the genus *Aconitum* wherein the composition contains 3 to 6 homeopathic pellets having a strength or potency of 3× or above (e.g., 4 standard, homeopathic pellets of 3× strength or above; note that 4× is a higher dilution than 3×, meaning that 4× is more diluted than 3×, but homeopathy considers 4× to be of a higher strength or potency than 3×).

3. A method of causing changes in the prefrontal cortex of the brain of a human or animal subject, by administering a composition containing at least one herb of the genus *Aconitum* wherein the composition contains 3 to 6 homeopathic pellets having a strength or potency of 3× or above (e.g., 4 standard homeopathic pellets of 3× strength or above).

4. A method of causing appropriate polarity switching and healthy right/left messaging in the prefrontal cortex in an animal or human subject by administering a composition containing at least one herb of the genus *Aconitum* wherein the composition contains 3 to 6 homeopathic pellets having a strength or potency of 3× or above (e.g., 4 standard homeopathic pellets of 3× strength or above).

5. A composition for the diagnosis and/or treatment of ADD/ADHD consisting essentially of an herb of the genus *Aconitum* wherein the composition contains 3 to 6 homeopathic pellets having a strength or potency of 3× or above (e.g., 4 standard homeopathic pellets of 3× strength or above).

6. A composition for the diagnosis and/or treatment of ADD/ADHD comprising an herb of the genus *Aconitum* wherein the composition contains 3 to 6 homeopathic pellets having a strength or potency of 3× or above (e.g., 4 standard homeopathic pellets of 3× strength or above) in combination with one or more vitamins, minerals, other herbs or other nutritional supplements.

7. A composition for the diagnosis and/or treatment of ADD/ADHD comprising primarily an herb of the genus *Aconitum* and a pharmaceutical grade stimulant such as Ritalin, Adderall or another compound or composition useful for the treatment of ADD/ADHD.

The compositions according to the invention may be used to diagnose an individual afflicted with ADD/ADHD, as follows.

The body is made of water and electricity. The brain works contralaterally, meaning that the right side of the brain sends electrical messages to the left side of the body, whereas the left side of the brain does the same to the right side of the body. This is called polarity. This electrical polarity can be switched so that the brain sends messages to the same side of the body in a homolateral manner.

The accepted test for polarity in Applied Kinesiology (referred to herein as "AK") is to check the K27 spots or 27th acupuncture points on the Kidney Meridian in Chinese medicine, which Applied Kinesiology is based on. If the human subject is electrically sound the muscle test or check should be strong. Muscle testing or checking has been proved empirically by Dr. Monti and it is the accepted way to electrically check bodily functions in AK. However, the polarity point which is on the bridge of the nose should test weak if the subject's electrical system is intact. It is well understood that if either the K27s show weakness and/or the polarity point shows strength then the subject has an electrical system that is referred to as "switched". This is well known in AK.

It is also well known in AK that the human body is made up of electricity. Because of this, one can muscle check different foods, medications, vitamins, and supplements by having the subject chew, chew and swallow, swish in the mouth without swallowing and/or drink the substance with 95% validity, smell it for 90% validity, and muscle test by placing the substance on the chest (between the shoulder and nipple below that shoulder) with 85% validity. The term "validity", refers to the accuracy of the muscle check test, so that 90% validity means that we can expect that there is a 10% margin of error if the substance is smelled. If the muscle test changes in the appropriate way, either weak or strong, with the substance then that substance will help the body in that particular area. Accordingly, that substance may be administered to the subject to heal or alleviate signs of illness or injury or dysfunction.

It is possible and well known in AK for a human subject to be switched due to physical trauma, emotional trauma and shock, lack of water, lack of sleep, lack of food, a sugar allergy, poisoning, and cranial faults. The present invention relates to the applicant's discovery that ADD/ADHD also causes switching. This is because in a human subject with ADD/ADHD, the prefrontal cortex of the brain is not always fully engaged with electricity. Therefore, especially when the subject attempts to focus or concentrate, the subject's electricity switches and the subject is unable to access his or her prefrontal cortex completely.

The applicant has also determined that it is possible to test a subject using any stimulant (e.g., caffeinated coffee, amphetamines such as methylphenidate (Ritalin®), nicotine, etc.) to determine whether the subject has ADD/ADHD, by determining whether switching is present. The muscle test will change in the appropriate direction only if the person suffers from ADD/ADHD. A weak K27 will become strong and/or a strong polarity point will become weak when tested with a stimulant or the homeopathic remedy of the present invention. Thus the polarity will only change by the muscle test if the subject has ADD/ADHD. (For example if the problem is lack of water (i.e., dehydration) then only water will fix the problem, not a stimulant). Because a person suffering from ADD/ADHD is typically at any given time polar or apolar, but may change from polar to apolar (and vice versa) over time, the test will only identify ADD/ADHD under the following conditions. First the person has to be switched or apolar at the time of the test and the stimulant has to change the muscle test in the appropriate way. If the person is polar it appears that it is not possible with this test to diagnose ADD/ADHD conclusively. However, people with ADD/ADHD easily switch and if you ask them to concentrate they most often become apolar, so that the condition may in fact be tested by this method. Prior to applicant's invention, this test was not known in the field.

Applicant's invention further relates to the discovery that the homeopathic agent *Aconitum napellus*, also referred to as Aconite, and which is derived from the Monkshood plant in the Genus of *Aconitum*, changes polarity in a human subject. Further, it also changes the polarity for people with ADD/ADHD, and further treats the conditions and symptoms of ADD/ADHD in a comparable manner to stimulants. This is done with virtually none of the side effects known to occur in some subjects when they are treated with stimulants.

The treatment requires 1-3 administrations per day of pellets consisting essentially of Aconite (i.e., does not contain other herbs or dietary supplements). Pharmaceutical stimulants currently used today are also typically administered 1-3 times per day. The dosage of each administration according to the invention will be comprised of 3 to 6 pellets or more (pellets are of a standard size known in homeopathy), each pellet having at least 3× strength.

In a preferred embodiment, administration will occur 2 to 3 times per day, and each administration will consist of at least 3 pellets of 3× strength.

In still yet another preferred embodiment, administration will occur 2 to 3 times per day, and each administration will consist of 5 pellets of 3× strength In yet another preferred alternative embodiment, administration will occur 2 to 3 times per day, and each administration will consist of at least 3 pellets of 6× strength.

In still yet another preferred embodiment, administration will occur 2 to 3 times per day, and each administration will consist of 5 pellets of 6× strength It is anticipated that 3 to 6 pellets, or even more than 6 pellets, may be administered each time, and that the strength may be varied from 3×, to 4× and beyond.

A further aspect of the present invention relates to a composition containing *Aconitum* and other herbs and dietary supplements. The composition would be administered in a capsule or other form, and would contain 5 pellets of 6× Aconitum GABA, Pycnogenol, and L-Tyrosine. In addition to the foregoing, the composition may also include one or more of the following: Ginko biloba, DMAE, Gotu Kola, Guarana, and/or L-5HTP.

In a preferred embodiment of the composition for use in the treatment of ADD/ADHD, a capsule containing the composition would contain 5 pellets of 6× *Aconitum napellus*, 50-500 mg GABA, and 200-500 mg of L-Tyrosine, and may optionally contain other herbs, amino acids, and other nutritional supplements. For example, the composition may contain chromium picolinate and/or other ingredients. This composition may be administered one to three times per day, and each administration would comprise one or two capsules.

As a substitute or in addition to the *Aconitum napellus*, *Aconitum carmichaeli* may be used. Still yet another Aconite which may be used is *Aconitum lycoc*.

An example of a specific preferred composition according to the inventions for the treatment of ADD/ADHD comprises the following ingredients in a capsule:

5 pellets of 6× *Aconitum napellus;*

50-500 mg GABA; and 200-500 mg L-tyrosine.

Thus, one aspect of the invention involves a dosage form, namely homeopathic pellets, which may be used to treat ADD/ADHD effectively and as comprehensively as a stimulant.

The treatment described herein is believed to activate the subject's brain's prefrontal cortex, resulting in the subject experiencing improved ability to focus/concentrate.

B. Depression

The compositions described above as useful for the treatment of ADD/ADHD may be administered orally as an antidepressant. As described above, the Aconite is administered in particularly defined quantities, i.e., at a dosage of 3 or 4 or more standard homeopathic pellets of 3× strength or above. Either Aconite alone as described above, or in combination with one or more other ingredients may be used. Examples of other ingredients of which may be used along with Aconite include: L-tryptophan, L-5HTP, serotonin, SAM-e and/or St. John's Wort. The Aconite and the one or more other ingredients may be administered in a single dosage form, such as via a single capsule containing the Aconite pellets and the one or more optional other ingredients. Alternatively, the Aconite and the one or more other ingredients may be administered simultaneously but via multiple and/or different dosage forms.

An example of a composition for the treatment of depression, according to the present invention would consist essentially of Aconite and St. John's Wort. A preferred embodiment would consist essentially of aconite in the dosage amounts described above with respect to the treatment of ADD/ADHD and about 250-600 mg of St. John's Wort. In yet another embodiment of the composition, additional ingredients such as 1-tryptophan, L-5HTP, serotonin, and/or SAM-e are included.

In a preferred embodiment, a composition for the treatment of depression comprises 5 6× pellets, and the St. John's Wort is present in an amount of about 600 mg.

C. Anxiety/Agitation

The compositions described above as useful for the treatment of ADD/ADHD may be administered orally as an anti-anxiety agent. As described above, the Aconite is administered in particularly defined quantities, i.e., at a dosage of 4 standard homeopathic pellets of 3× strength or above. Either Aconite alone as described above, or in combination with one or more other ingredients may be used. Examples of other ingredients of which may be used along with Aconite include GABA, melatonin, Kava kava and valerian root. The Aconite and the one or more other ingredients may be administered in a single dosage form, such as via a single capsule containing the Aconite and the one or more other ingredients. Alternatively, the aconite and the one or more other ingredients may be administered simultaneously but via multiple and/or different dosage forms.

An example of a composition for the treatment of anxiety, according to the present invention would consist essentially of aconite, GABA and melatonin A preferred composition would consist essentially of aconite in the dosage amounts described above with respect to the treatment of ADD/ADHD, about 300 mg GABA and about 2 mg of kava kava. Alternatively, the composition would further include Kava kava, valerian root and/or chromium picolinate.

A preferred composition for the treatment of anxiety according to the invention comprises GABA, Glycine, Magnesium, Taurine and Kava kava. The preferred amounts of each are at least 50 mg GABA, at least 10 mg of Glycine, at least 25 mg Magnesium, at least 25 mg of Taurine, and at least 25 mg of Kava kava. In a preferred embodiment, the composition contains 6× pellets of Aconite, plus about 500 mg GABA, about 25 mg Glycine, about 100 mg Magnesium, about 250 mg Taurine, and about 150 mg Kava kava.

D. Memory Disorders, Including but not Limited to Alzheimer's Disease

The compositions described above as useful for the treatment of ADD/ADHD may be administered orally for the treatment of memory disorders, including but not limited to Alzheimer's Disease. As described above, the aconite is administered in particularly defined quantities, i.e., at a dosage of 3-4 or more standard homeopathic pellets of 3× strength or above. Either aconite alone as described above, or in combination with one or more other ingredients may be used. Examples of other ingredients of which may be used along with Aconite include L-tyrosine, Guarana, Ginkgo biloba and Gotu kola. The aconite and the one or more ingredients may be administered in a single dosage form, such as via a single capsule containing the Aconite and the one or more other ingredients. Alternatively, the Aconite and the one or more other ingredients may be administered simultaneously but via multiple and/or different dosage forms.

An example of a composition for the treatment of memory disorders, according to the present invention would consist essentially of aconite and tyrosine. Alternatively, the composition would further include Guarana, Ginkgo biloba and/or Gotu kola.

A further example of a composition for the treatment of memory disorders according to the invention comprises Ginkgo Biloba, L-tyrosine, Inositol, Taurine, and Phosphatidyl serine.

A preferred embodiment contains about 100 mg Ginkgo Biloba, about 335 mg L-tyrosine, about 200 mg Inositol, about 200 mg Taurine, and about 100 mg of Phosphatidyl serine.

E. Menopausal Symptoms

The compositions described above for use in the treatment of memory problems are proposed to be used also for the treatment of menopausal symptoms, such as mood swings, fatigue, depression, sleep problems and mental clarity. As described above, the aconite is administered in particularly defined quantities, i.e., at a dosage of 3 or 4 or more standard homeopathic pellets of 3× strength or above.

F. Obsession, Including Obsessive-Compulsive Disorder

The compositions described above as useful for the treatment of ADD/ADHD may be administered orally as for the treatment of obsessive behavior and/or obsessive thoughts. As described above, the aconite is administered in particularly defined quantities, i.e., at a dosage of 3 or 4 standard homeopathic pellets of 3× strength or above. Either aconite alone as described above, or in combination with one or more other ingredients may be used. Examples of other ingredients of which may be used along with Aconite include: GABA, Kava kava, and L-5HTP. The aconite and the one or more other ingredients may be administered in a single dosage form, such as via a single capsule containing the Aconite and the one or more other ingredients. Alternatively, the Aconite and the one or more other ingredients may be administered simultaneously but via multiple and/or different dosage forms.

An example of a composition for the treatment of depression, according to the present invention would consist essentially of Aconite, GABA, kava kava and L-5HTP. A preferred embodiment would consist essentially of aconite in the dosage amounts described above with respect to the treatment of ADD/ADHD and about 250 mg of GABA, about 100 mg of Kava kava, and about 100 mg of L-5HTP.

An example of a composition for the treatment of obsessive disorders according to the invention consists essentially of Magnesium and Kava kava. A preferred embodiment contains about 750 mg GABA, about 100 mg Magnesium, and about 150 mg Kava kava G. Sleep Disorders, Including Insomnia The compositions described above as useful for the treatment of ADD/ADHD may be administered orally as for the treatment of sleep disorders, such as promoting falling asleep, staying asleep and/or improving the quality of sleep. As described above, the aconite is administered in particularly defined quantities, i.e., at a dosage of 3 or 4 standard homeopathic pellets of 3× strength or above. Either aconite alone as described above, or in combination with one or more other ingredients may be used. Examples of other ingredients of which may be used along with aconite for this purpose include: GABA, melatonin, kava kava, and/or valerian root. The aconite and the one or more other ingredients may be administered in a single dosage form, such as via a single capsule containing the aconite and the one or more other ingredients. Alternatively, the aconite and the one or more other ingredients may be administered simultaneously but via multiple and/or different dosage forms.

An example of a composition for the treatment of sleep disorders, according to the present invention would consist essentially of aconite and GABA. A preferred embodiment would consist essentially of aconite in the dosage amounts described above with respect to the treatment of ADD/ADHD and about 500 mg of GABA and about 2 mg of melatonin Optionally, the aforementioned embodiment could be revised to also include kava kava and/or valerian root.

H. Prostate and Bladder Enhancement

Aconite may be used in the amounts described herein with respect to the treatment of ADD/ADHD. As described above, the aconite is administered in particularly defined quantities, i.e., at a dosage of 3 or 4 standard homeopathic pellets of 3× strength or above.

I. Aphrodisiac Uses

The compositions described above as useful for the treatment of ADD/ADHD may be administered orally as for enhancing and/or increasing sexual desire and/or enhancing sexual performance and/or stamina. As described above, the aconite is administered in particularly defined quantities, i.e., at a dosage of 3 or 4 more standard homeopathic pellets of 3× strength or above. Either aconite alone as described above, or in combination with one or more other ingredients may be used. Examples of other ingredients of which may be used along with aconite as an aphrodesiac include: yohimbe, ginseng, L-tyrosine, GABA and/or pycgenol. Preferably the composition contains all of the foregoing ingredients. Still more preferably, the composition will include about 50 mg of GABA. The aconite and the one or more other ingredients may be administered in a single dosage form, such as via a single capsule containing the aconite and the one or more other ingredients. Alternatively, the aconite and the one or more other ingredients may be administered simultaneously but via multiple and/or different dosage forms.

DETAILED DESCRIPTION OF THE DRAWINGS

SPECT scans measure the function of the brain, by measuring the blood flow to areas of the brain. The areas of the brain showing "hollows" or "holes" are those areas having minimal blood flow thereto. These "hollows" or "holes" are indicative of portions of the brain which are not functioning as they would in a "normal" or "typical" human brain.

FIGS. 1A-1F illustrate a series of SPECT scans of a 36 year old female human subject, showing the effects of treatment according to the invention and according to the prior art. During each scan the Conner's ADD test was administered. During the first scan the subject missed 15.11, in the second scan she missed 4.51, and in the third scan she missed 10.67, so it appears that the performance of the composition according to the invention surpassed Adderall significantly.

FIG. 1A shows the typical prefrontal cortex of an ADD patient who is concentrating without any medication. It clearly shows the deep pockets where the brain has essentially gone to sleep and is unable to focus.

FIG. 1B shows the same brain and the same concentration task with two capsules of the supplement according to the invention. The left lobe is almost completely smooth, the right lobe has improved by 40-50%, and the whole brain is smoother and fuller.

FIG. 1C shows a scan while the subject was concentrating, after administering 20 mg of Adderall. The left lobe is not quite as good as that shown in FIG. 1B but the right lobe is about 40% better. The composition of the invention performed at roughly 75% to 85% as well as the Adderall for prefrontal activity.

Figures 1D, 1E, 1F:
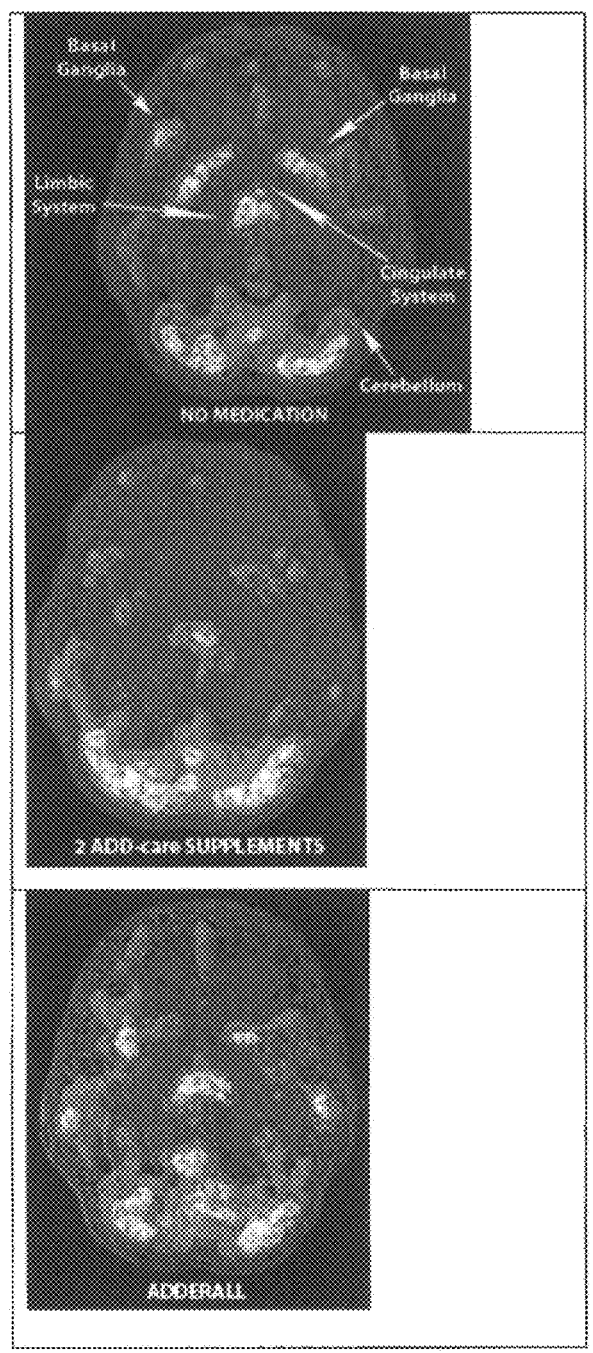

FIG. 1D illustrates a deep view of the same patient scans. This first scan is the same concentration scan without medication. The white areas show any part of the brain that is working 15% greater than it should optimally. However the bottom part of the brain or cerebellum is different and should be completely filled in with white suggesting dopamine activity. The two large white areas on either side of center are the basal ganglia. The middle section is the limbic system. The cingulate system often appears like a Mohawk haircut running up and down the full length of the middle of the brain. At the top of the limbic system the small white area indicates that the cingulate system is also over activated.

FIG. 1E illustrates the effect of administration of a composition according to the invention, and it clearly shows that there is much more involvement in the cerebellum. With ADD-care the basal ganglia and cingulate system have cleared dramatically and the limbic system has been reduced by at least 80-90%. This may explain why subjects feel calm as well as focused when they have been administered the composition according to the invention.

FIG. 1F illustrates the subject having been administered Adderall. It has 90% of cerebellum activity compared to the composition of the invention. The basal ganglia, limbic, and cingulate system though are still quite pronounced and that may be cause a lot of the side effects that people see with the stimulants. The composition according to the invention performed significantly better.

FIGS. 2A-2F illustrate a series of SPECT scans of a 44 year old female human subject, showing the effects of treatment according to the invention and according to the prior art.

Figures 2A, 2B, 2C:
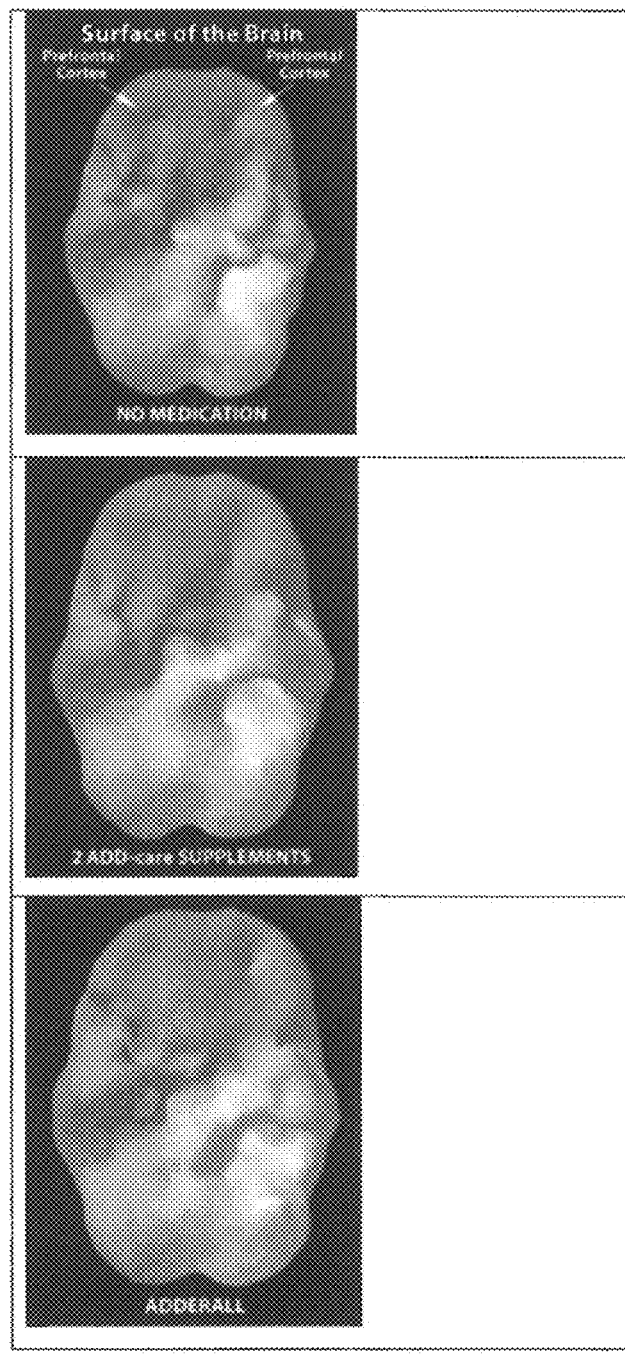
FIGS. 2A-2F illustrate a series of SPECT scans of a 44 year old female human subject, showing the effects of treatment according to the invention and according to the prior art.

FIG. 2A shows the unmedicated SPECT scan of a 44 year old woman suffering from over-focused ADD. Both hemispheres of the prefrontal cortex show the deep pockets that are typical for ADD. These pockets depict decreased blood flow which results in a lack of focus and impulsivity.

FIG. 2B illustrates a surface scan of the same woman having been administered the composition according to the invention. The pockets are gone and the two hemispheres are smooth and symmetrical which indicates tremendous improvement of her ADD.

FIG. 2C shows a surface scan with the subject after administration of 20 mg. of Adderall. The left lobe is smooth and regular, but the right lobe has a deep pocket showing decreased activity. The composition according to the invention appears to have been at least 20% more effective in the prefrontal cortex area.

Figures 2D, 2E, 2F:
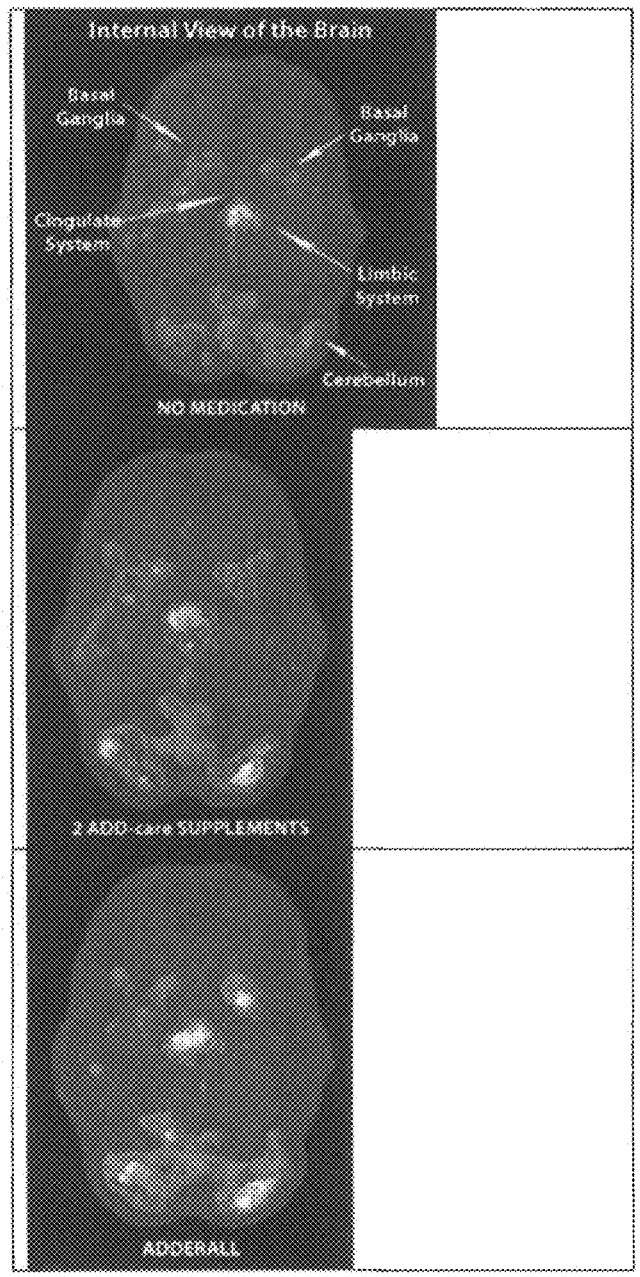

FIG. 2D shows a scan of the subject unmedicated, but shows the deeper part of her brain. There is only a sliver of white in the cerebellum at the bottom. There is some basal ganglia inflammation on the left and significant problems in the limbic system. The inflammation in the limbic system is also large enough to indicate an inflammation in the cingulate system.

FIG. 2E shows the subject after administration of the composition according to the invention (3 capsules, each containing 5 pellets of 6× Aconite, 165 mg GABA and 335 mg L-Tyrosine, and shows significant improvement in the cerebellum. The rest of the brain shows essentially no change from the unmedicated scan.

FIG. 2F shows a deep scan of the subject on 20 mg Adderall. The limbic system is 5-10% more inflamed than on the ADD-care scan and the right basal ganglia is impaired while the scan of 3E had full functioning. The right cerebellum shows 15% less functioning for Adderall while the left lobe was 5-10% less effective with the Adderall.

FIGS. 3A-3F illustrate a series of SPECT scans of a 58 year old female human subject, showing the effects of treatment according to the invention and according to the prior art. The subject had complaining of memory problems, challenges with direction, difficulty learning, and time management issues since childhood. Since menopause these problems had become worse and she had become lethargic as well. During each scan the Conner's ADD test was administered. During the first scan the subject missed 4.44, the second scan missed 4.44, and the third scan the patient missed 4.44, so there was no difference noted on performance between the three groups. However, the subject stated subjectively that she was more focused and calm with the composition according to the invention.

Figures 3A, 3B, 3C:
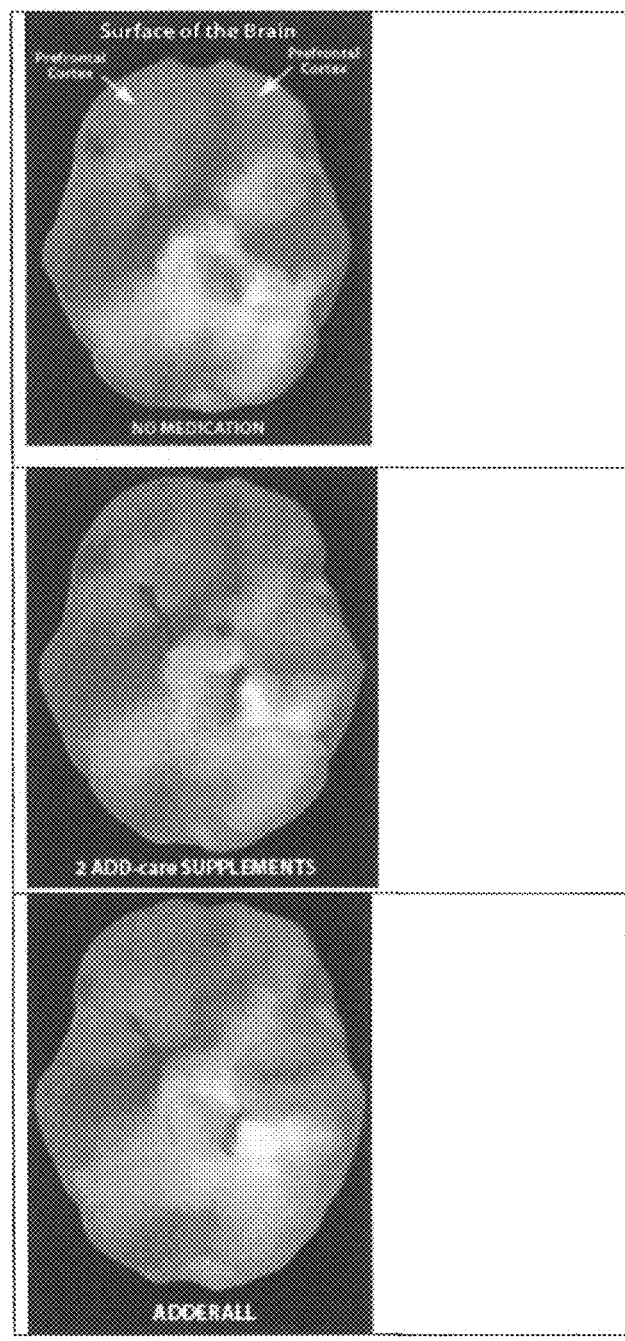
FIGS. 3A-3F illustrate a series of SPECT scans of a 58 year old female human subject, showing the effects of treatment according to the invention and according to the prior art.

FIG. 3A is a surface scan without medication and with concentration did not show the typical ADD pattern of pockets in the prefrontal cortex, but did show a very slight indentation in the right side.

FIG. 3B this shows a scan after administration of the composition according to the invention, and showed essentially the same pattern as the first scan (FIG. 3A) with a slight indentation in the right lobe.

FIG. 3C shows a surface scan after administration of Adderall, and showed the same pattern as in FIG. 3B.

Figures 3D, 3E, 3F:
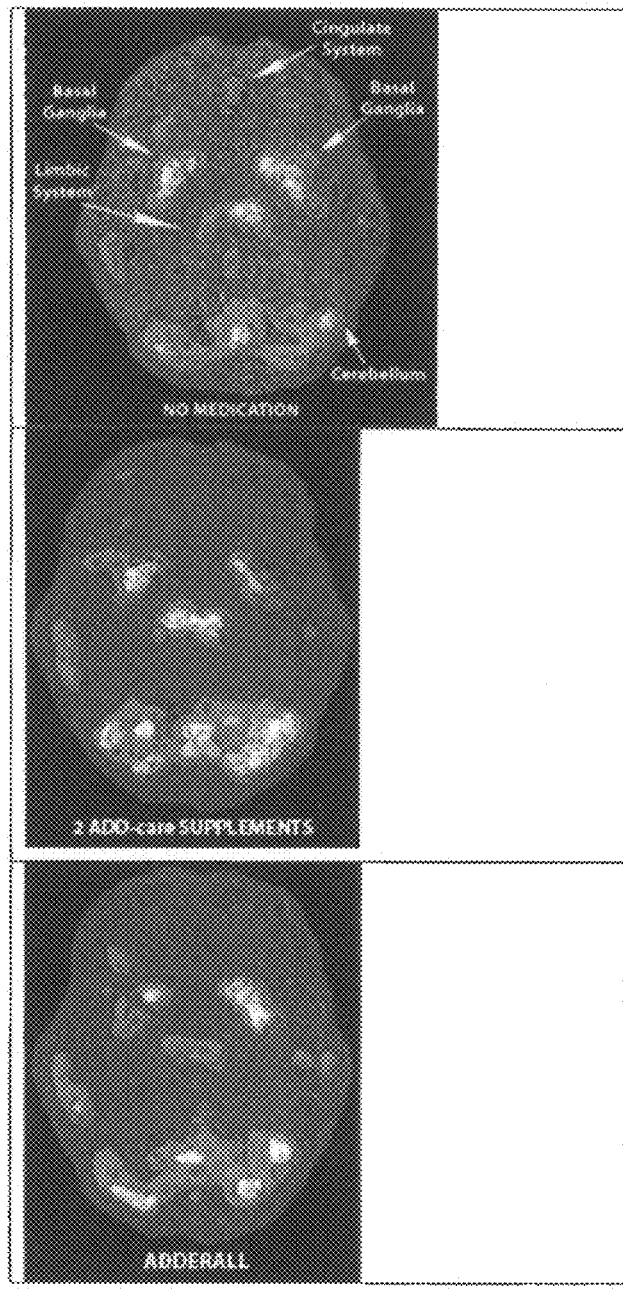

FIG. 3D shows a deep scan with no medication and concentration showed very little activity in the cerebellum, which meant that very little dopamine was present. Dopamine depletion is a huge component in attention deficit disorder and memory. The limbic system is inflamed and both basal ganglia are quite enlarged showing depression and anxiety.

FIG. 3E shows a deep scan after administration of a composition according to the invention, and showed a huge improvement in dopamine in the cerebellum. The basal ganglia on the left was reduced by 60% and the one on the right was reduced by 75%. The limbic system was increased by 50%.

FIG. 3F shows a deep scan after administration of Adderall, and reflects only moderate improvement in the cerebellum from the first scan and not nearly as good as the composition according to the invention. The limbic system was significantly improved however versus the composition of the invention. Basal ganglia activity on the left was 70% better with Adderall, but the right was 75% better with the composition according to the invention.

What is claimed is:

1. A method for treating attention deficit hyperactivity disorder, comprising orally administering to a human subject affected with said disorder a composition comprising 10 homeopathic pellets of Aconite wherein each pellet is of 6× strength, about 50-500 mg of GABA and about 200-500 mg of L-tyrosine.

2. The method of claim 1, wherein the composition further comprises one or more nutritional supplements.

3. The method of claim 2, wherein the composition further comprises one or more nutritional supplements selected from the group consisting of pycnogenol, Ginko biloba, DMAE, Gotu kola, Guarana, L-5HTP, magnesium, and zinc.

4. The method of claim 1, wherein the composition comprises about 165 mg of GABA and about 335 mg of L-tyrosine.

5. The method of claim 2, wherein the composition comprises about 165 mg of GABA and about 335 mg of L-tyrosine.

6. The method of claim 3, wherein the composition comprises about 165 mg of GABA and about 335 mg of L-tyrosine.

7. A method for activating the prefrontal cortex of the brain in a human or mammal subject, comprising orally administering to the subject a composition comprising 10 homeopathic pellets of Aconite wherein each pellet is of 6× strength, about 50-500 mg of GABA and about 200-500 mg of L-tyrosine.

8. A homeopathic method for treating attention deficit hyperactivity disorder, comprising orally administering to a human subject affected with said disorder a composition comprising 15 homeopathic pellets of Aconite wherein each pellet is of 6× strength, about 50-500 mg of GABA and about 200-500 mg of L-tyrosine.

9. The method of claim 7, wherein the composition comprises about 165 mg of GABA and about 335 mg of L-tyrosine.

10. The method of claim 8, wherein the composition comprises about 165 mg of GABA and about 335 mg of L-tyrosine.

11. A method for treating attention deficit hyperactivity disorder, comprising orally administering to a human subject affected with said disorder a composition comprising 15 homeopathic pellets of Aconite wherein each pellet is of 6× strength, about 50-500 mg of GABA and about 200-500 mg of L-tyrosine.

12. The method of claim 11, wherein the composition further comprises one or more nutritional supplements.

13. The method of claim 12, wherein the composition further comprises one or more nutritional supplements selected from the group consisting of pycnogenol, Ginko biloba, DMAE, Gotu kola, Guarana, L-5HTP, magnesium, and zinc.

14. The method of claim 11, wherein the composition comprises about 165 mg of GABA and about 335 mg of L-tyrosine.

* * * * *

UNITED STATES PATENT AND TRADEMARK OFFICE
CERTIFICATE OF CORRECTION

| | | |
|---|---|---|
| PATENT NO. | : 8,545,810 B2 | Page 1 of 1 |
| APPLICATION NO. | : 13/314112 | |
| DATED | : October 1, 2013 | |
| INVENTOR(S) | : Jef Gazley | |

It is certified that error appears in the above-identified patent and that said Letters Patent is hereby corrected as shown below:

In the specification,

Column 3, line 60, delete "L-Tyrosine" and insert --L-tyrosine-- therefor.

Column 6, lines 30 and 37, delete each occurrence of "L-Tyrosine" and insert --L-tyrosine-- therefor.

Column 8, lines 45 and 66, delete each occurrence of "kava kava" and insert --Kava kava-- therefor.

Column 8, line 54, delete "Kava kava" and insert --Kava kava.-- therefor.

Column 9, line 11, delete "melatonin" and insert --melatonin.-- therefor.

Column 9, line 13, delete "kava kava" and insert --Kava kava-- therefor.

Column 10, line 61, delete "L-Tyrosine," and insert --L-tyrosine),-- therefor.

Column 11, line 6, delete "subject had complaining" and insert --subject had been complaining-- therefor.

Signed and Sealed this
First Day of March, 2016

Michelle K. Lee
*Director of the United States Patent and Trademark Office*